US012089965B2

(12) United States Patent
Hu et al.

(10) Patent No.: US 12,089,965 B2
(45) Date of Patent: Sep. 17, 2024

(54) SBL-BASED SSR BRAIN SOURCE LOCALIZATION METHOD

(71) Applicant: SOOCHOW UNIVERSITY, Suzhou (CN)

(72) Inventors: Nan Hu, Suzhou (CN); Mingwen Qu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 797 days.

(21) Appl. No.: 17/285,087

(22) PCT Filed: Jul. 30, 2020

(86) PCT No.: PCT/CN2020/105690
§ 371 (c)(1),
(2) Date: Apr. 13, 2021

(87) PCT Pub. No.: WO2021/135205
PCT Pub. Date: Jul. 8, 2021

(65) Prior Publication Data
US 2022/0125385 A1 Apr. 28, 2022

(30) Foreign Application Priority Data
Jan. 2, 2020 (CN) .......................... 202010001431.5

(51) Int. Cl.
*A61B 5/00* (2006.01)
*A61B 5/291* (2021.01)
(Continued)

(52) U.S. Cl.
CPC ............ *A61B 5/7267* (2013.01); *A61B 5/374* (2021.01); *A61B 5/38* (2021.01); *A61B 5/7203* (2013.01);
(Continued)

(58) Field of Classification Search
CPC ...... G06N 7/01; A61B 5/7203; A61B 5/7257; A61B 5/291; A61B 5/7267; A61B 5/38; A61B 5/374; G16H 30/20
See application file for complete search history.

(56) References Cited

U.S. PATENT DOCUMENTS

| 8,483,816 B1 * | 7/2013 | Payton .................. A61B 34/30 |
| | | 700/245 |
| 9,247,890 B2 * | 2/2016 | Turnbull .............. A61B 5/4094 |
| 2017/0065199 A1 * | 3/2017 | Meisel ................. A61B 5/4094 |

FOREIGN PATENT DOCUMENTS

| CN | 104688222 A | 6/2015 |
| CN | 108802683 A | 11/2018 |
| CN | 110251083 A * | 9/2019 |

(Continued)

OTHER PUBLICATIONS

Vangelis et a., "A Novel Bayesian for EEG Source Localization", pp. 1-12, vol. 2020, Research Arrticle (Year: 2020).*

(Continued)

*Primary Examiner* — Michael J Dalbo
*Assistant Examiner* — Kaleria Knox
(74) *Attorney, Agent, or Firm* — SZDC Law PC

(57) ABSTRACT

The invention discloses a sparse Bayesian learning (SBL)-based SSR brain source localization method. An SSR record is divided into multiple data segments, frequency-domain information of the data segments is extracted through FFT, and a data matrix is constructed. An automatic iteration stop condition and initial values of a sparse support vector and a spontaneous electroencephalography (EEG)-electrical noise joint power vector are set. The posteriori mean and covariance of SSR components are iteratively estimated and the sparse support vector and the spontaneous EEG-electrical noise joint power vector are updated accordingly. When the iteration ends, the ultimate sparse support vector is used to (Continued)

give a source localization result. An SSR source localization problem is modeled in the frequency domain, the joint sparsity of signals in multiple data segments is involved, and a brain source localization method applicable to various SSRs is given in an SBL framework.

5 Claims, 4 Drawing Sheets

(51) Int. Cl.
*A61B 5/374* (2021.01)
*A61B 5/38* (2021.01)
*G06N 7/01* (2023.01)
*G06N 20/00* (2019.01)
*G16H 30/20* (2018.01)

(52) U.S. Cl.
CPC .............. *A61B 5/7257* (2013.01); *G06N 7/01* (2023.01); *G06N 20/00* (2019.01); *G16H 30/20* (2018.01); *A61B 5/291* (2021.01)

(56) References Cited

FOREIGN PATENT DOCUMENTS

| | | |
|---|---|---|
| CN | 111096745 A | 5/2020 |
| WO | WO-2011058059 A1 * | 5/2011 ......... A61B 5/04012 |
| WO | 2019182915 A1 | 9/2019 |

OTHER PUBLICATIONS

Nan Hua et al., "Source localization for sparse array using non-negative sparse Bayesian learning" Signal Processing 127 (2016) 37-43 (Mar. 3, 2016).

* cited by examiner the joint localization result of the plurality of subjects:
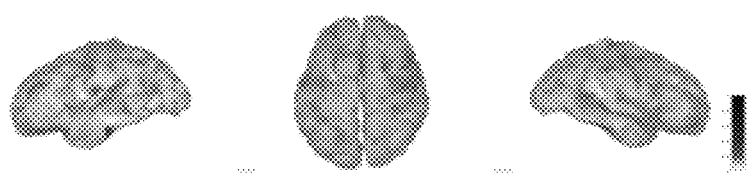

the localization result of the subject 1:
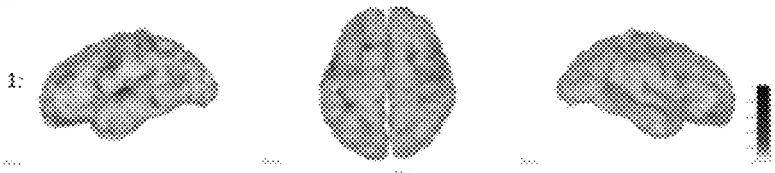

the localization result of the subject 2:
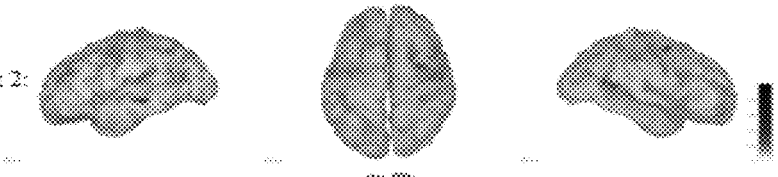

the localization result of the subject 3:
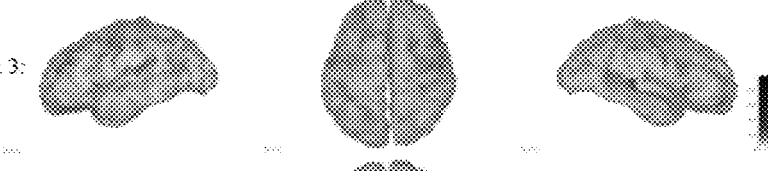

the localization result of the subject 4:
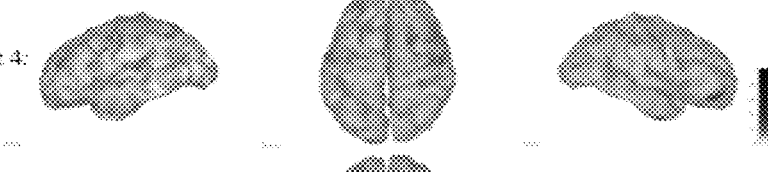

the localization result of the subject 5:
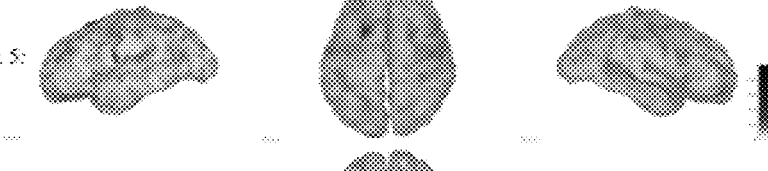

the localization result of the subject 6:
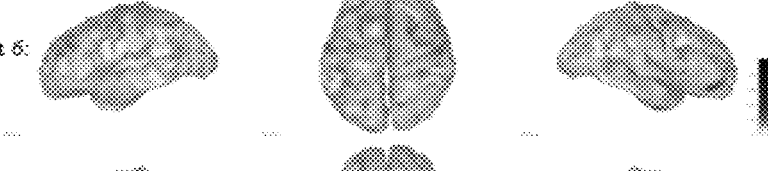

the localization result of the subject 7:
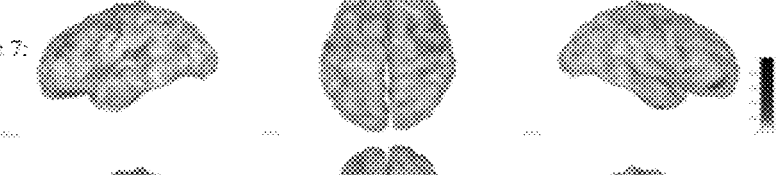

the localization result of the subject 8:
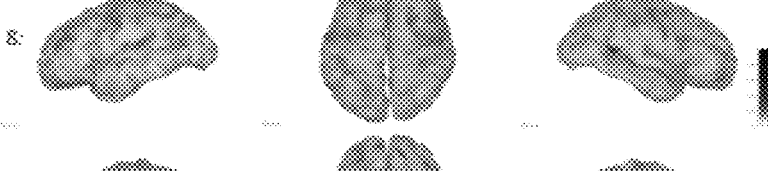

the localization result of the subject 9:
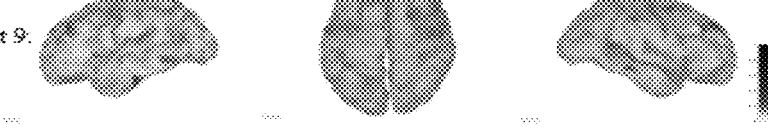

*FIG. 6*

SBL-BASED SSR BRAIN SOURCE LOCALIZATION METHOD

This application is the National Stage Application of PCT/CN2020/105690, filed on Jul. 30, 2020, which claims priority to Chinese Patent Application No. 202010001431.5, filed on Jan. 2, 2020, which is incorporated by reference for all purposes as if fully set forth herein.

FIELD OF THE INVENTION

The present invention relates to the field of steady-state responses (SSRs), and more particularly to a sparse Bayesian learning (SBL)-based SSR brain source localization method.

DESCRIPTION OF THE RELATED ART

An SSR is an electroencephalography (EEG) signal component evoked by a periodic stimulation signal and has a sine signal form whose frequency is the same as the frequency of the periodic stimulation signal. Compared with a transient evoked potential, an SSR has the advantage that it is easy to use Fourier analysis to distinguish between a signal and noise in the frequency domain. At present, the research on SSRs mainly focuses on fields such as the auditory, visual, and somatosensory fields, and has significant potential application value in the medical field. For example, an auditory SSR is generated by periodic auditory stimulation and may be used for listening tests, monitored anesthesia care, and neurological assessment, and a visual SSR may be correlated to the operation mode of attention of a subject.

To explain the basic mechanism of a cognitive process from the perspective of an EEG source signal origination is a problem that urgently needs to be resolved. An EEG record acquired by electrodes on the scalp may reflect the activity of neurons in the brain. The proper modeling of the relationship between the EEG record and the electrophysiological activity of neurons becomes the key to the solution of the brain source localization problem. After decades of researches, a lot of researches have been done on brain source localization. For the selection of a source model, a distributed source model is usually preferred. Compared with an equivalent current dipole model, the number of sources is not assumed in the distributed source model, and better localization accuracy can be achieved. During the use of the distributed source model, the estimation of the spatial distribution of activated neurons by using observed EEG data is a severely underdetermined inverse problem. To constrain the solution space, suitable a priori assumptions need to be introduced. In a conventional linear distribution method, fixed and known a priori assumptions are usually used. A priori assumptions that are subjectively set significantly affect the accuracy of source localization results. To obtain more suitable a priori conditions from the perspective of data, the Bayesian inference methods were introduced into the brain source localization problem in an increasing number of studies. A priori assumptions are embedded in the form of prior distributions in a Bayesian framework, and they are further evaluated by the Bayesian inference process.

Although an SSR source localization problem may be simplified in the frequency domain by using Fourier analysis as an SSR has sparse features in the frequency domain, at present, no such study has been done to propose a source localization method for an SSR. Hence, based on the features of an SSR in the frequency domain, it is of great significance to establish a brain source localization method applicable to an SSR in the Bayesian framework.

At present, no published patent applications have solved the SSR brain source localization problem based on SBL. However, some papers have proposed some SBL-based methods to solve brain source localization problems for transient evoked potentials, for example:

The literature *A unified Bayesian framework for MEG/EEG source imaging* by Wipf and Nagarajan analyzed and extended several types of Bayesian methods applicable to a source localization problem, including the empirical Bayesian method, standard MAP estimation, and multivariable variational Bayesian approximation, wherein improvements were made in combination with existing methods, and a unified Bayesian framework applicable to EEG/MEG source imaging was proposed.

The literature *Evaluating the Performance of BSBL methodology for EEG Source Localization On a Realistic Head Model* by Saha, et al. and *Bayesian EEG Source Localization Using a Structured Sparsity Prior* by Costa, et al. proposed that structural sparsity further needs to be considered to improve the performance of source localization algorithms, and introduced internal block structural information and multivariable Bernoulli-Laplacian structured sparsity priori in a Bayesian framework, respectively.

In combination with the status quo of current researches, the application of a Bayesian method to the brain source localization problem has great advantages. However, practical and feasible methods further need to be proposed for the application to SSR brain source localization.

Conventional technologies have the following technical problems:

1. A priori assumptions or empirical parameters need to be subjectively set, and hence source localization performance were significantly restricted or affected.
2. SSR frequency domain information was not fully used to perform source localization analysis.
3. The joint sparsity between data segments was not fully used.
4. In the case of a low signal-to-noise ratio, source localization results had low spatial resolution.

SUMMARY OF THE INVENTION

A technical problem to be solved by the present invention is to provide a sparse Bayesian learning (SBL)-based steady-state response (SSR) brain source localization method, to solve: (1) how to model an SSR brain source localization problem in the frequency domain; (2) how to estimate the positions of neural sources completely based on acquired EEG record data without presetting empirical parameters or variables; (3) how to perform source localization by fully exploiting the joint sparsity among multiple segments of SSR EEG data; and (4) how to achieve more accurate SSR brain source localization result in a low signal-to-noise ratio condition.

To solve the foregoing technical problem, the present invention provides an SBL-based SSR brain source localization method, including:

step 1. dividing an SSR scalp record acquired by M electrodes into L segments of data, and preprocessing the L segments of data to increase a signal-to-noise ratio, to obtain L data segments $x_l(t)$, where l=1, 2, ... L;

step 2. performing fast Fourier transform (FFT) on $x_l(t)$ corresponding to the L data segments, extracting a complex component $\tilde{x}_l$ of $x_l(t)$ at a stimulation frequency $f_0$, integrating it corresponding to the L data segments to form a matrix X containing joint SSR distribution information on multiple data segments, where $X=[\tilde{x}_1, \tilde{x}_2, \ldots \tilde{x}_L]^T$, $(\bullet)^T$ represents transpose, and if there is data of a plurality of subjects, horizontally arranging data matrices of the subjects into one matrix X;

step 3. setting parameters of an iteration program: an iteration threshold $\varepsilon$ and a maximum number of iterations $N_{iter}$, and initializing variables in the iteration program: initializing a sparse support vector $\alpha$ as $\alpha_{init}$, and initializing a spontaneous EEG-electrical noise joint power vector $\gamma$ as $\gamma_{init}$;

step 4. calculating a posteriori mean vector $\mu_l$ and a posteriori covariance matrix $\Sigma_l$ of a source signal corresponding to an $l^{th}$ segment of data, by using an SSR data information matrix X, a lead-field matrix (LFM) $\tilde{L}$ corresponding to the head model and electrode montage, an old sparse support vector $\alpha$, and the spontaneous EEG-electrical noise joint power vector $\gamma$;

step 5. calculating updated values $\alpha_{new}$ and $\gamma_{new}$ of the sparse support vector $\alpha$ and the spontaneous EEG-electrical noise joint power vector $\gamma$ by using $\mu_l$ and $\Sigma_l$;

step 6. determining whether an iteration stop condition is satisfied: the number of iterations $n \geq N_{iter}$ or $$\frac{\|\alpha_{new} - \alpha\|_2}{\|\alpha\|_2} \leq \varepsilon,$$

where if the iteration stop condition is not satisfied, make $\alpha=\alpha_{new}$ and $\gamma=\gamma_{new}$, and the process returns to step 4 to continue to perform iteration, or otherwise, iteration ends, and the sparse support vector $\alpha$ is outputted, to obtain a source localization result.

In an embodiment, preprocessing the data includes performing baseline correction and averaging on the overlapped data.

In an embodiment, initializing variables in the iteration program includes:
(1) initializing the sparse support vector $\alpha$ as $\alpha_{init} = \Sigma_{l=1}^L \rho_l^* \odot \rho_l / L$, where $\rho_l = \sqrt{N} \tilde{L}^H \tilde{x}_l / \|\tilde{L}^H \tilde{L}\|_F$, $(\bullet)^H$ represents conjugate transpose, $\odot$ represents a Hadamard product, and $\|\bullet\|_F$ represents a Frobenius norm; and
(2) initializing a spontaneous EEG-electrical noise joint power $\gamma_l$ corresponding to the $l^{th}$ segment of data as $\gamma_{init,l} = (\tilde{x}_l - \tilde{L}\rho_l)^H(\tilde{x}_l - \tilde{L}\rho_l)/M$, where $l=1, 2, \ldots, L$.

In an embodiment, calculating $\mu_l$ and $\Sigma_l$ by using an SSR data information matrix X, an LFM $\tilde{L}$ corresponding to the head model and electrode montage, an old sparse support vector $\alpha$, and the spontaneous EEG-electrical noise joint power vector $\gamma$ includes:

$$\Sigma_l = \Lambda - \Lambda \tilde{L}^H (\gamma_l I_M + \tilde{L} \Lambda \tilde{L}^H)^{-1} \tilde{L} \Lambda, \text{ where } \Lambda = \text{diag}(\alpha); \text{ and} \quad (1)$$

$$\mu_l = \gamma_l^{-1} \Sigma_l \tilde{L}^H \tilde{x}_l. \quad (2)$$

In an embodiment, calculating updated values $\alpha_{new}$ and $\gamma_{new}$ of the sparse support vector $\alpha$ and the spontaneous EEG-electrical noise joint power vector $\gamma$ by using $\mu_l$ and $\Sigma_l$ includes:
(1) $\alpha_{new}[n] = \Sigma_{l=1}^L (\Sigma_l[n, n] + \mu_l[n]\mu_l[n]^*)/L$, where $n=1, 2, \ldots, N$, $\alpha_{new}[n]$ is an $n^{th}$ element of $\alpha_{new}$, $(\bullet)^*$ represents a conjugate operation, $\Sigma_l[n, n]$ is an $(n, n)^{th}$ element of $\Sigma_l$, and $\mu_l[n]$ is an $n^{th}$ element of $\mu_l$; and (2)

$$\gamma_{new}[l] = \frac{\tilde{x}_l^H \tilde{x}_l - 2\text{Re}(\tilde{x}_l^H \tilde{L} \mu_l) + tr\left[\tilde{L}^H \tilde{L}\left(\Sigma_l + \mu_l \mu_l^H\right)\right]}{M},$$

where $l=1, 2, \ldots, L$, $\gamma_{new}[l]$ is an $l^{th}$ element of $\gamma_{new}$, and $\text{Re}(\bullet)$ and $tr(\bullet)$ are respectively calculating the real part and performing trace operation.

In an embodiment, calculating the LFM $\tilde{L}$ corresponding to the head model and electrode montage includes:
(1) using a boundary element method (BEM) or a finite element method (FEM) to calculate a 3-layer real head model formed by the scalp, skull, and cortex;
(2) using N evenly distributed triangle meshes to represent the spatial positions of distributed dipoles on the surface of the cortex; and
(3) calculating, in combination with the spatial location information of the M connected EEG acquisition electrodes on the scalp and by using OpenMEEG software, the LFM $\tilde{L}$ based on the real head model, where the size of the matrix is M×N, and subsequently the matrix may be saved for repeated use.

An SBL-based SSR brain source localization apparatus includes: a computer, the computer is programmed to perform the following steps:

step 1. dividing an SSR scalp record acquired by M electrodes into L segments of data, and preprocessing the L segments of data to increase a signal-to-noise ratio, to obtain L data segments $x_l(t)$, where $l=1, 2, \ldots L$;

step 2. performing FFT on $x_l(t)$ corresponding to the data segments, extracting a complex component $\tilde{x}_l$ of $x_l(t)$ at a stimulation frequency $f_0$, integrating $\tilde{x}_l$ corresponding to the L data segments into a matrix X of joint SSR multi-data segment structure information, where $X=[\tilde{x}_1, \tilde{x}_2, \ldots \tilde{x}_L]^T$, $(\bullet)^T$ represents transpose, and if there is data of a plurality of subjects, horizontally arranging data matrices of the subjects into one matrix X;

step 3. setting parameters of an iteration program: an error threshold $\varepsilon$ and a maximum number of iterations $N_{iter}$, and initializing variables in the iteration program: initializing a sparse support vector $\alpha$ to $\alpha_{init}$, and initializing a spontaneous EEG-electrical noise joint power vector $\gamma$ to $\gamma_{init}$;

step 4. calculating a posteriori mean vector $\mu_l$ and a posteriori covariance matrix $\Sigma_l$ of a source signal corresponding to an $l^{th}$ segment of data by using an SSR data information matrix X, an LFM $\tilde{L}$ corresponding to the distribution of head models and electrodes, an old sparse support vector $\alpha$, and the spontaneous EEG-electrical noise joint power vector $\gamma$;

step 5. calculating updated values $\alpha_{new}$ and $\gamma_{new}$ of the sparse support vector $\alpha$ and the spontaneous EEG-electrical noise joint power vector $\gamma$ according to $\mu_l$ and $\Sigma_l$; and step 6. determining whether an iteration stop condition is satisfied: the number of iterations $n \geq N_{iter}$ or $$\frac{\|\alpha_{new} - \alpha\|_2}{\|\alpha\|_2} \leq \varepsilon,$$

where if the iteration stop condition is not satisfied, it is assumed that $\alpha = \alpha_{new}$ and $\gamma = \gamma_{new}$, and the process returns to step 4 to continue to perform iteration, or otherwise, iteration ends, and the sparse support vector α is outputted, to obtain a source localization result.

In an embodiment, preprocessing the data includes performing baseline correction and overlapping averaging on the data.

In an embodiment, initializing variables in the iteration program includes:
(1) initializing the sparse support vector α to $\alpha_{init} = \Sigma_{l=1}^{L} \rho_l * \odot \rho_l / L$, where $\rho_l = \sqrt{N}\tilde{L}^H \tilde{x}_l / \|\tilde{L}^H \tilde{L}\|_F$, e represents a Hadamard product, and $\|\cdot\|_F$ represents a Frobenius norm; and
(2) initializing a spontaneous EEG-electrical noise joint power $\gamma_l$ corresponding to the $l^{th}$ segment of data to $\gamma_{init,l} = (\tilde{x}_l - \tilde{L}\rho_l)^H (\tilde{x}_l - \tilde{L}\rho_l)/M$, where l=1, 2, ..., L.

In an embodiment, calculating $\mu_l$ and $\Sigma_l$ by using an SSR data information matrix X, an LFM L corresponding to the distribution of head models and electrodes, an old sparse support vector α, and the spontaneous EEG-electrical noise joint power vector γ includes:

$$\Sigma_l = \Lambda - \Lambda \tilde{L}^H (\gamma_l I_M + \tilde{L}\Lambda\tilde{L}^H)^{-1} \tilde{L}\Lambda, \text{ where } \Lambda = \text{diag}(\alpha); \text{ and} \quad (1)$$

$$\mu_l = \gamma_l^{-1} \Sigma_l \tilde{L}^H \tilde{x}_l. \quad (2)$$

In an embodiment, calculating updated values $\alpha_{new}$ and $\gamma_{new}$ of the sparse support vector α and the spontaneous EEG-electrical noise joint power vector γ according to $\mu_l$ and $\Sigma_l$ includes:
(1) $\alpha_{new}[n] = \Sigma_{l=1}^{L}(\Sigma_l[n, n] + \mu_l[n]\mu_l[n]^*)/L$, where n=1, 2, ..., N, $\alpha_{new}[n]$ is an $n^{th}$ element of $\alpha_{new}$, $(\cdot)^*$ represents a conjugate operation, $\Sigma_l[n, n]$ is an $(n, n)^{th}$ element of $\Sigma_l$, and $\mu_l[n]$ is an $n^{th}$ element of $\mu_l$; and
(2)

$$\gamma_{new}[l] = \frac{\tilde{x}_l^H \tilde{x}_l - 2Re(\tilde{x}_l^H \tilde{L}\mu_l) + tr[\tilde{L}^H \tilde{L}(\sum_l + \mu_l \mu_l^H)]}{M},$$

where l=1, 2, ..., L, $\gamma_{new}[l]$ is an $l^{th}$ element of $\gamma_{new}$, and Re(•) and tr(•) are respectively calculating the real part and performing trace operation.

In an embodiment, calculating the LFM $\tilde{L}$ corresponding to head model and electrode montage includes:
(1) using a BEM or an FEM to calculate a 4-layer real head model formed by the scalp, skull, cerebrospinal fluid, and cortex;
(2) using N evenly distributed triangle meshes to represent the spatial positions of distributed dipoles on the surface of the cortex; and
(3) calculating, in combination with the spatial location information of the M connected EEG acquisition electrodes on the scalp and by using OpenMEEG software, an LFM $\tilde{L}$ based on the real head model, where the size of the matrix is M×N, and subsequently the matrix may be saved for repeated use.

The beneficial effects of the present invention are as follows:
(1) In the present invention, an SSR source localization problem is modeled in the frequency domain according to frequency-domain characteristics of an SSR.
(2) In the present invention, the joint sparsity of SSR sources among multiple data segments is used, and an obtained SSR source localization result has better generality.
(3) In the present invention, the estimation of a sparse support vector and a spontaneous EEG-electrical noise power is learned in a data-driven iteration process without setting any a priori condition according to experience.
(4) In the present invention, multiple data segments are joined together to improve SSR source localization performance in a low signal-to-noise ratio condition.

BRIEF DESCRIPTION OF THE DRAWINGS

FIG. 6 is a diagram of localization performances for 40-Hz auditory SSR sources calculated by using the SBL-based SSR brain source localization method according to the present invention.

DETAILED DESCRIPTION OF THE PREFERRED EMBODIMENTS

The present invention is further illustrated below with reference to the accompanying drawings and specific embodiments, to enable a person skilled in the art to better understand and implement the present invention. However, the embodiments are not intended to limit the present invention.

The present invention intends to establish an SBL-based SSR source localization algorithm according to frequency domain characteristics of an SSR. An SSR record is first divided into multiple data segments, and frequency domain information of the data of the SSR record is extracted by using FFT. In an SBL framework, an SSR source localization problem is modeled in the frequency domain. In combination with the joint sparsity of SSR sources among data segments, a sparse support vector is used to constrain a solution space, and an expectation-maximization (EM) algorithm is eventually used to implement a data-driven iteration process to learn a sparse support vector, hence obtaining an SBL algorithm applicable to the SSR brain source localization problem.

It may be understood that an SBL-based SSR brain source localization method is the same as the steps that a computer is programmed to perform in the SBL-based SSR brain source localization apparatus based on the same inventive concept. Only the SBL-based SSR brain source localization method is described below in detail.

Figure 1:
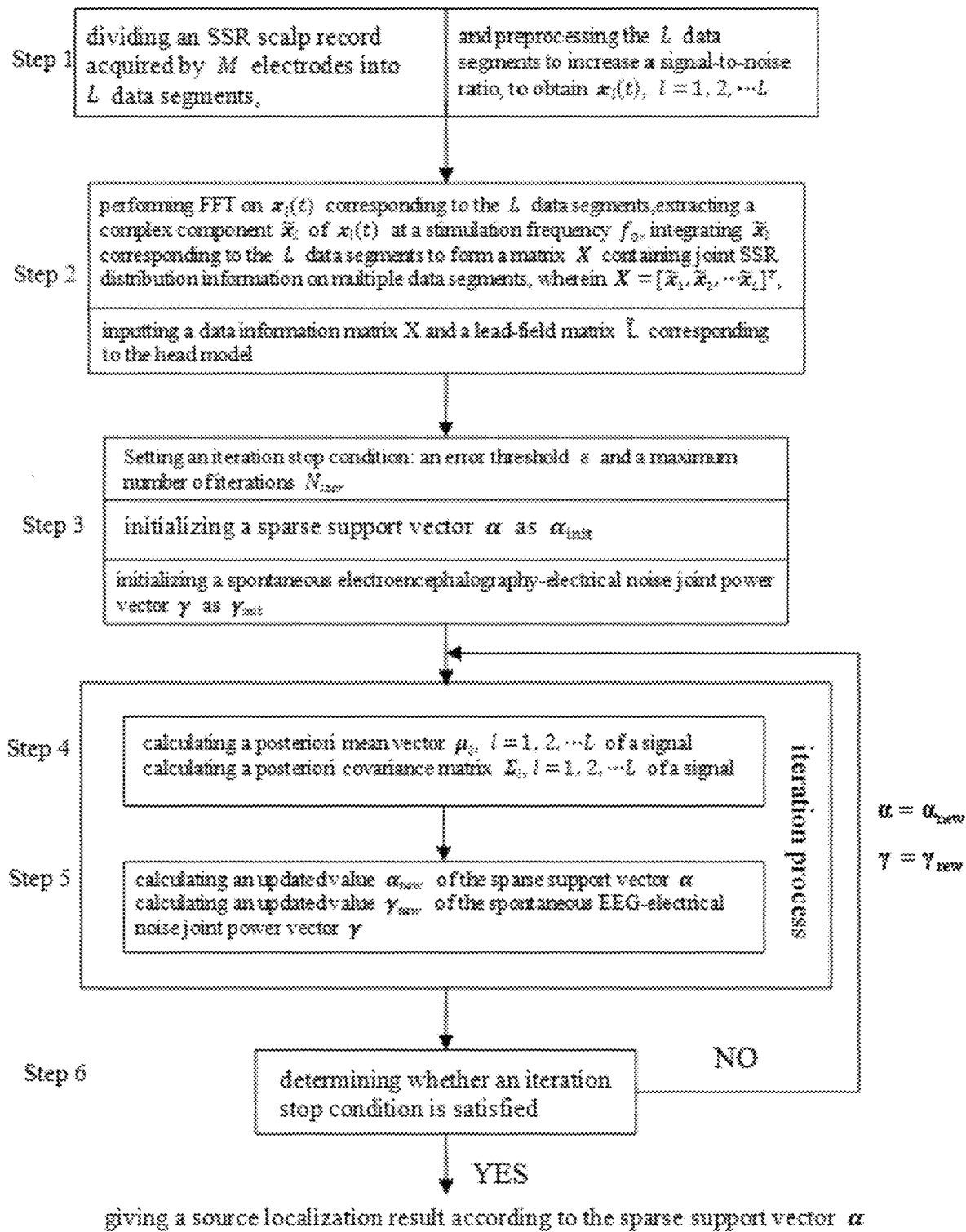
FIG. 1 is a flowchart of an SBL-based SSR brain source localization method according to the present invention.

The technical solution of the present invention is shown in a flowchart in FIG. 1.

A sparse Bayesian learning-based SSR brain source localization method includes:
step 1. dividing an SSR scalp record acquired by M electrodes into L segments of data, and preprocessing the L segments of data to increase a signal-to-noise ratio, to obtain L data segments $x_l(t)$, where l=1, 2, ... L;

step 2. performing FFT on $x_l(t)$ corresponding to the L data segments, extracting a complex component $\tilde{x}_l$ of $x_l(t)$ at a stimulation frequency $f_0$, integrating $\tilde{x}_l$ corresponding to the L data segments to form a matrix X containing joint SSR distribution information on multiple data segments, where $X=[\tilde{x}_1, \tilde{x}_2, \ldots \tilde{x}_L]^T$, $(\bullet)^T$ represents transpose, and if there is data of a plurality of subjects, horizontally arranging data matrices of the subjects into one matrix X;

step 3. setting parameters of an iteration program: an error threshold $\varepsilon$ and a maximum number of iterations $N_{iter}$, and initializing variables in the iteration program: initializing a sparse support vector $\alpha$ as $\alpha_{init}$, and initializing a spontaneous EEG-electrical noise joint power vector $\gamma$ as $\gamma_{init}$;

step 4. calculating a posteriori mean vector $\mu_l$ and a posteriori covariance matrix $\Sigma_l$ of a source signal corresponding to an $l^{th}$ segment of data, by using an SSR data information matrix X, an LFM $\tilde{L}$ corresponding to the head model and electrode montage, an old sparse support vector $\alpha$, and the spontaneous EEG-electrical noise joint power vector $\gamma$;

step 5. calculating updated values $\alpha_{new}$ and $\gamma_{new}$ of the sparse support vector $\alpha$ and the spontaneous EEG-electrical noise joint power vector $\gamma$ by using $\mu_l$ and $\Sigma_l$;

step 6. determining whether an iteration stop condition is satisfied: the number of iterations $n \geq N_{iter}$ or $$\frac{\|\alpha_{new} - \alpha\|_2}{\|\alpha\|_2} \leq \varepsilon,$$

where if the iteration stop condition is not satisfied, make $\alpha = \alpha_{new}$ and $\gamma = \gamma_{new}$, and the process returns to step 4 to continue to perform iteration, or otherwise, iteration ends, and the sparse support vector $\alpha$ is outputted, to obtain a source localization result.

1. Preprocessing the data includes performing baseline correction and overlapping averaging on the data.
2. Initializing variables in the iteration program includes:
(1) initializing the sparse support vector $\alpha$ to $\alpha_{init} = \Sigma_{l=1}^L \rho_l^* \odot \rho_l / L$, where $\rho_l = \sqrt{N} \tilde{L}^H \tilde{x}_l / \|\tilde{L}^H \tilde{L}\|_F$, $(\bullet)^H$ represents conjugate transpose, $\odot$ represents a Hadamard product, and $\|\bullet\|_F$ represents a Frobenius norm; and
(2) initializing a spontaneous EEG-electrical noise joint power $\gamma_l$ corresponding to the $l^{th}$ segment of data to $\gamma_{init,l} = (\tilde{x}_l - \tilde{L}\rho_l)^H(\tilde{x}_l - \tilde{L}\rho_l)/M$, where l=1, 2, ..., L.
3. Calculating $\mu_l$ and $\Sigma_l$ by using an SSR data information matrix X, an LFM $\tilde{L}$ corresponding to the distribution of head models and electrodes, an old sparse support vector $\alpha$, and the spontaneous EEG-electrical noise joint power vector $\gamma$ includes:

$$\Sigma_l = \Lambda - \Lambda \tilde{L}^H (\gamma_l I_M + \tilde{L} \Lambda \tilde{L}^H)^{-1} \tilde{L} \Lambda, \text{ where } \Lambda = \text{diag}(\alpha); \text{ and} \quad (1)$$

$$\mu_l = \gamma_l^{-1} \Sigma_l \tilde{L}^H \tilde{x}_l. \quad (2)$$

4. Calculating updated values $\alpha_{new}$ and $\gamma_{new}$ of the sparse support vector $\alpha$ and the spontaneous EEG-electrical noise joint power vector $\gamma$ according to $\mu_l$ and $\Sigma_l$ includes:
(1) $\alpha_{new}[n] = \Sigma_{l=1}^L (\Sigma_l[n,n] + \mu_l[n]\mu_l[n]^*)/L$, where n=1, 2, ..., N, $\alpha_{new}[n]$ is an $n^{th}$ element of $\alpha_{new}$, $(\bullet)^*$ represents a conjugate operation, $\Sigma_l[n,n]$ is an $(n,n)^{th}$ element of $\Sigma_l$, and $\mu_l[n]$ is an $n^{th}$ element of $\mu_l$; and (2)

$$\gamma_{new}[l] = \frac{\tilde{x}_l^H \tilde{x}_l - 2Re(\tilde{x}_l^H \tilde{L} \mu_l) + tr[\tilde{L}^H \tilde{L}(\Sigma_l + \mu_l \mu_l^H)]}{M},$$

where l=1, 2, ..., L, $\gamma_{new}[l]$ is an $l^{th}$ element of $\gamma_{new}$, and $Re(\bullet)$ and $tr(\bullet)$ are respectively calculating the real part and performing trace operation.

Appendix: The present invention relates to a theoretical derivation process of an SBL algorithm (1) Signal Model An SSR is evoked by a periodic stimulation signal and has the form of a sinusoidal signal. The frequency of the SSR is the same as that of the frequency of the stimulation signal. It is assumed that an SSR is evoked by a stimulation signal whose frequency is $f_0$. K aroused currents in the sinusoidal form, that is, $s_1(t), s_2(t), \ldots, s_K(t)$, are generated on the cortex. Within a particular time frame, these signals are relatively stable and have the following forms:

$$s_k(t) = a_k \sin(2\pi f_0 t + \varphi_k), k=1,2,\ldots,K, \quad (1)$$

where $a_k$ and $\varphi_k$ represent the amplitude and phase of $s_k(t)$, respectively. According to Euler's formula, $s_k(t)$ may further be decomposed into two parts:

$$s_k(t) = \frac{a_k}{2} e^{j\varphi_k} e^{j2\pi f_0 t} - j\frac{a_k}{2} e^{-j\varphi_k} e^{-j2\pi f_0 t}, \quad (2)$$

$$k = 1, 2, \ldots, K.$$

For an EEG record within a long-time stimulation, in the present invention, it may be assumed that the amplitude of an SSR basically remains constant within a short time but may change after this time slice. With this assumption, if the entire record is divided into multiple segments, the $K^{th}$ source signal in the $l^{th}$ data segment may be represented as:

$$s_{k,l}(t) = \tilde{s}_{k,l} e^{j2\pi f_0 t} + \hat{s}_{k,l} e^{-j2\pi f_0 t}, \quad (3)$$

where $\tilde{s}_{k,l}$ and $\hat{s}_{k,l}$ represent the weights corresponding to complex components $e^{j2\pi f_0 t}$ and $e^{-j2\pi f_0 t}$, respectively.

The EEG record acquired on the scalp is generated from a conduction process of neuronal electric activity by using a real head model. A classic head model usually includes three layers having different conductivities, including the cortex, skull, and scalp. In such a electric signal transmission process, the weight of dipole current activity may be modeled by using an LFM $L_0$. The LFM may be calculated by using FEM or BEM. If the M electrodes are used in EEG acquisition, when a type of periodic stimulation evokes an SSR, an EEG signal $x_l(t)$ in the $l^{th}$ data segment may be represented in a vector form:

$$x_l(t) = \Sigma_{k=1}^K L_0(r_k) \psi_k s_{k,l}(t) + \xi_l(t) + n_l(t), \quad (4)$$

where $L_0(r_k)$ is an LFM component of the $k^{th}$ source at the position $r_k$, and $\psi_k$ is a directional vector including three elements and is used to represent the current direction of the $k^{th}$ source. $\xi_l(t)$ and $n_l(t)$ respectively represent spontaneous EEG and electrical noise included in the $l^{th}$ data segment, respectively. In practice, spontaneous EEG may also be represented by the mapping of neuronal activity by using the LFM. However, in the problem of localizing neuronal activity related to an SSR, spontaneous EEG is considered as interference.

If only the neuronal activity on the surface of the cortex is focused on, because pyramidal neurons are perpendicular to the surface of the cortex, the model represented by Formula (4) may further be simplified into:

$$x_l(t)=Ls_l(t)+\xi_l(t)+n_l(t), \quad (5)$$

where, the $k^{th}$ column of the LFM, corresponding to the $k^{th}$ source, is $L[:,k]=L(r_k) \triangleq L_0(r_k)\psi(r_k)$, directional vectors $\psi_1$, $\psi_2$, ..., $\psi_K$ of sources are represented by $\psi(r_1)$, $\psi(r_2)$, ..., $\psi(r_K)$, respectively, $s_l(t) \triangleq [s_{1,l}(t), s_{2,l}(t), \ldots, s_{K,l}(t)]^T$ represents an SSR signal waveform generated by K sources, and the symbol $(\cdot)^T$ represents transpose. Formula (3) is substituted into Formula (5) to obtain:

$$x_l(t)=L\tilde{s}_l e^{j2\pi f_0 t}+L\hat{s}_l e^{-j2\pi f_0 t}+\xi_l(t)+n_l(t), \quad (6)$$

where $\tilde{s}_l=[\tilde{s}_{1,l}, \tilde{s}_{2,l}, \ldots, \tilde{s}_{K,l}]^T$, and $\hat{s}_l=[\hat{s}_{1,l}, \hat{s}_{2,l}, \ldots, \hat{s}_{K,l}]^T$.

Time-frequency analysis is performed on acquired EEG data. For example, FFT is performed on the $l^{th}$ segment of data, and the component of the data at the stimulation frequency $f_0$ is then extracted. According to Formula (6), the component $\tilde{x}_l$ at $f_0$ in the EEG record may be represented as:

$$\tilde{x}_l = L\tilde{s}_l + \tilde{\xi}_l + \tilde{n}_l, l=1,2,\ldots,L, \quad (7)$$

where $\tilde{\xi}_l$ and $\tilde{n}_l$ represent the components of $\xi_l(t)$ and $n_l(t)$ at the frequency $f_0$, respectively. It is assumed that $\tilde{s}_l$ may be variant or invariant among data segments, and $\tilde{n}_l$ always follows a complex Gaussian distribution having a fixed variance $\sigma_n^2$, that is, $\tilde{n}_l \sim CN(0, \sigma_n^2)$. Assuming that the spontaneous EEG component $\tilde{\xi}_l$ satisfies the complex Gaussian distribution, to make the model more realistic, it is considered that the variance $\sigma_l^2$ may change among data segments, that is:

$$\tilde{\xi}_l \sim CN(0,\sigma_l^2), l=1,2,\ldots,L, \quad (8),$$

where $\sigma_l^2$ follows a gamma distribution, that is, $\tilde{\xi}_l$ follows a K-distribution.

(2) Hierarchical Bayesian Model

To solve the SSR source localization problem presented in Formula (7), an appropriate Bayesian network first needs to be established. In (7), it is assumed that $\tilde{\xi}_l$ and $\tilde{n}_l$ satisfy Gaussian distributions with a variant variance and a variance being fixed, respectively. Because $\tilde{\xi}_l$ and $\tilde{n}_l$ are independent of each other, $e_l \triangleq \tilde{\xi}_l + \tilde{n}_l \sim CN(0, \sigma_l^2 + \sigma_n^2)$. If $\gamma_l \triangleq \sigma_l^2 + \sigma_n^2$ and $\tilde{s}_l$ are given, $\tilde{x}_l$ satisfies a Gaussian distribution, whose mean is $L\tilde{s}_l$, the and variance is $\gamma_l$, that is, the conditional distribution of $\tilde{x}_l$ can be represented as:

$$p(\tilde{x}_l \mid L\tilde{s}_l, \gamma_l) = CN(\tilde{x}_l \mid L\tilde{s}_l, \gamma_l I) = \frac{1}{\pi^M \gamma_l^M}\exp\left[-\frac{(\tilde{x}_l - L\tilde{s}_l)^H(\tilde{x}_l - L\tilde{s}_l)}{\gamma_l}\right], \quad (9)$$

where $(\cdot)^H$ represents conjugate transpose. In combination with $\tilde{x}_l$, where $l=1, 2, \ldots L$ corresponding to the L segments of data, and the matrix X containing multi-segment joint structure information can be obtained. Furthermore, because when $m \neq n$, $\tilde{x}_m \mid \tilde{s}_m, \gamma_m$ is not correlated to $\tilde{x}_n \mid \tilde{s}_n, \gamma_n$, the conditional distribution of X can be represented as:

$$p(X \mid LS, \gamma) = \prod_{l=1}^{L} p(\tilde{x}_l \mid L\tilde{s}_l, \gamma_l) = \prod_{l=1}^{L} CN(\tilde{x}_l \mid L\tilde{s}_l, \gamma_l I) = \prod_{l=1}^{L} \frac{1}{\pi^M \gamma_l^M}\exp\left[-\frac{(\tilde{x}_l - L\tilde{s}_l)^H(\tilde{x}_l - L\tilde{s}_l)}{\gamma_l}\right]. \quad (10)$$

Here, $S=[\tilde{s}_1, \tilde{s}_2, \ldots, \tilde{s}_L]$, and $\gamma=[\gamma_1, \gamma_2, \ldots, \gamma_L]^T$.

Because the position of an SSR activation source is still unknown at present, a search should be performed in the range of the entire cortex. If the entire cortex is evenly divided into N meshes, the positions of sources corresponding to the meshes are represented by $\tilde{r}_1, \tilde{r}_2, \ldots, \tilde{r}_N$, so that an LFM with the size of M×N obtained after the source space is extended can be represented as $\tilde{L}=[L_0(\tilde{r}_1)\psi(\tilde{r}_1), L_0(\tilde{r}_2)\psi(\tilde{r}_2), \ldots, L_0(\tilde{r}_N)\psi(\tilde{r}_N)]$. Generally, in the process in which the periodic stimulation signal arouses an SSR, only a few neurons on the cortex are activated, that is, K<N. Therefore, a row sparse matrix W of N×L is defined in the present invention to represent active source strength corresponding to N source positions distributed on the entire cortex, so that $LS=\tilde{L}W$. When one source of an SSR is just located at the $n^{th}$ source position, that is, $r_k=\tilde{r}_n$, $r_k \in \{r_1, r_2, \ldots, r_K\}$, the component $W[n,:]$ corresponding to W at the $n^{th}$ source position corresponds to the strength of the $k^{th}$ SSR activation source, that is, $W[n,:]=S[k,:]$, or otherwise, the elements of $W[n,:]$ should all be 0. Provided that $\tilde{r}_1, \tilde{r}_2, \ldots, \tilde{r}_N$ are determined, $\tilde{L}$ can be predetermined, and the conditional distribution of X in (10) is transformed into:

$$p(X \mid W, \gamma) = \prod_{l=1}^{L} p(\tilde{x}_l \mid w_l, \gamma_l) = \prod_{l=1}^{L} CN(\tilde{x}_l \mid \tilde{L}\tilde{w}_l, \gamma_l I) = \prod_{l=1}^{L} \frac{1}{\pi^M \gamma_l^M}\exp\left[-\frac{(\tilde{x}_l - \tilde{L}\tilde{w}_l)^H(\tilde{x}_l - \tilde{L}\tilde{w}_l)}{\gamma_l}\right], \quad (11)$$

where $w_l$ is the $l^{th}$ column of W.

For an SSR with a determined type, the position of an activation source would have no significant change among data segments, resulting in the row sparsity of W. The joint sparsity among columns of W may be provided by modeling. That is, the columns of W follow the same complex Gaussian distribution, that is:

$$p(w_l \mid \alpha) = CN(w_l \mid 0, \text{diag}(\alpha)), l=1,2,\ldots L, \quad (12)$$

where the vector $\alpha$ of size N×1 is a common variance vector, an entry with a relatively large value in $\alpha$ represents that the SSR active source is more likely to be located at a corresponding position, when $l \neq l'$, $w_l \mid \alpha$ and $w_{l'} \mid \alpha$ are independent of each other, so that the conditional distribution of W may be represented as:

$$p(w \mid \alpha) = \prod_{l=1}^{L} p(w_l \mid \alpha) = \prod_{l=1}^{L} CN(w_l \mid 0, \text{diag}(\alpha)) = \prod_{l=1}^{L} \prod_{n=1}^{N} \frac{1}{\pi \alpha_n}\exp\left(-\frac{|w_{n,l}|^2}{\alpha_n}\right) \quad (13)$$

where $w_{n,l}$ represents the $(n,l)^{th}$ element of W. It may be found out that $\alpha$ controls the row sparsity of W. Therefore, if $\alpha$ is accurately estimated, the positions of SSR active sources can be given.

In (11) and (13), $\gamma$ and $\alpha$ are considered as random variable vectors. In the following analysis, they will be deemed as parameters instead. That is, $p(X \mid W, \gamma)$ in (11) and $p(W \mid \alpha)$ in (13) are replaced with $p(X \mid W; \gamma)$ and $p(W; \alpha)$, respectively, and the parameters $\gamma$ and $\alpha$ will be the targets of Bayesian inference.

A. Bayesian Network Under the Condition of a Single Subject

For a single subject, a joint probability distribution $p(X, W; \gamma, \alpha)$ may be represented by a product of multiplying conditional distributions $p(X \mid W; \gamma)$ and $p(W; \alpha)$:

$$p(X, W; \gamma, \alpha) = p(X \mid W; \gamma) p(W; \alpha), \quad (14)$$

where W is considered as a hidden variable matrix in Bayesian inference.

B. Bayesian Network Under the Condition of Multiple Subjects

To exploit the common source positions of an SSR of a determined type, SSR arousing experiments are usually performed on multiple subjects. In SBL, the distribution of common sources can be learned by using a data collection of multiple subjects. If a total of P subjects have participated in SSR arousing experiments, an extended data matrix extracted at the frequency $f_0$ is represented by $X=[X_1, X_2, \ldots, X_P]$, where the data matrix $X_p$ of the $p^{th}$ subject may be formed by $L_p$ column vectors. Similarly, in the present invention, $W=[W_1, W_2, \ldots, W_P]$ and $\gamma=[\gamma_1^T, \gamma_2^T, \ldots, \gamma_P^T]^T$ are also defined. Under the condition of multiple subjects, the joint SSR activation source localization may be modeled by using the row sparsity of W, that is, the sparsity shared by $W_1, W_2, \ldots, W_P$, i.e.

$$p(W;\alpha)=\Pi_{p=1}^{P}p(W_p;\alpha)=\Pi_{p=1}^{P}\Pi_{l_p=1}^{L_p}p(W_{p,l_p};\alpha)=\Pi_{p=1}^{P}\Pi_{l_p=1}^{L_p}CN(W_{p,l_p}|0,\text{diag}(\alpha)), \quad (15)$$

where $\alpha$ is used to control the same sparsity among $W_1$, $W_2, \ldots$, and $W_P$. When $p_1 \neq p_2$, $X_{p_1}|W_{p_1};\gamma_{p_1}$ and $X_{p_2}|W_{p_2};\gamma_{p_2}$ are independent of each other, and therefore $p(X|W;\gamma)=\Pi_{p=1}^{P}p(X_p|W_p;\gamma_p)$. At this time, it can be obtained that $p(X,W;\gamma,\alpha)=p(X|W;\gamma)p(W;\alpha)$, which is the same as that obtained under the condition of a single subject in (14). Therefore, the same SBL method is applicable to the scenario of a single subject as well as the scenario of multiple subjects.

(3) SBL

Based on the Bayesian model established above, the EM algorithm may be used to derive parameters $\gamma$ and $\alpha$. The premise of applying EM is deriving the posteriori distribution of the hidden variable matrix in the model, that is, $p(W|X;\gamma,\alpha)$. According to the Bayesian rule, it may be obtained that:

$$p(w_l|x_l;\gamma,\alpha)=CN(w_l|\mu_l,\Sigma_l), l=1,2,\ldots,L, \quad (16)$$

where $\mu_l=\gamma_l^{-1}\Sigma_l\tilde{L}^H\tilde{x}_l$, $\Sigma_l=(\Lambda^{-1}+\gamma_l^{-1}\tilde{L}^H\tilde{L})^{-1}$, and $\Lambda=\text{diag}(\alpha)$. Furthermore, because when $l \neq l'$, $w_l|x_l;\gamma,\alpha$ and $w_{l'}|x_{l'};\gamma,\alpha$ are independent of each other, it may be obtained that:

$$p(W|X;\gamma,\alpha)=\Pi_{l=1}^{L}p(w_l|x_l;\gamma,\alpha). \quad (17)$$

In the process of EM, by maximizing the conditional expectation $E_{p(W|X;\gamma,\alpha)}\{\log p(X,W;\gamma,\alpha)\}$, parameter vectors $\gamma$ and $\alpha$ may be iteratively learned. Furthermore, because $\log p(X,W;\gamma,\alpha)=\log p(X|W;\gamma)+\log p(W;\alpha)$, and $\log p(X|W;\gamma)$ is not correlated to $\alpha$, in the process of deriving $\alpha$, it is only necessary to maximize:

$$Q(\alpha)=E_{p(W|X;\gamma,\alpha)}\{\log p(W;\alpha)\}. \quad (18)$$

The partial derivative of $\alpha_n$ in $Q(\alpha)$ is calculated, so that an updated value of $\alpha$ can be obtained by:

$$\alpha_n = \frac{\sum_{l=1}^{L} E_{p(W|X;\gamma,\alpha)}\{|w_{n,l}|^2\}}{L} = \sum_{l=1}^{L}\left(\sum_{l}[n,n]+\mu_l[n]\mu_l[n]^*\right)/L, \quad (19)$$

$n=1,2,\ldots N,$ where $(\bullet)^*$ represents the conjugate operation, $\Sigma_l[n,n]$ represents the $(n,n)^{th}$ element of $\Sigma_l$, and $\mu_l[n]$ is the $n^{th}$ element of $\mu_l$. Similarly, because $\log p(W;\alpha)$ is not correlated to $\gamma$, $\gamma$ may be derived from the process of maximizing $Q(\gamma)$, where $$Q(\gamma)=E_{p(W|X;\gamma,\alpha)}\{\log p(X|W;\gamma)\}. \quad (20)$$

The partial derivative of $\gamma_l$ in $Q(\gamma)$ is calculated, so that an updated value of $\gamma$ may be obtained:

$$\gamma_l = \frac{E_{p(W|X;\gamma,\alpha)}\{(\tilde{x}_l-\tilde{L}w_l)^H(\tilde{x}_l-\tilde{L}w_l)\}}{M} = \frac{\tilde{x}_l^H\tilde{x}_l-2Re(\tilde{x}_l^H\tilde{L}\mu_l)+tr[\tilde{L}^H\tilde{L}(\sum_l+\mu_l\mu_l^H)]}{M}, l=1,2,\ldots L, \quad (21)$$

where $Re(\bullet)$ and $tr(\bullet)$ respectively represent calculating the real part and calculating trace of a matrix, respectively.

In the SBL algorithm proposed in the present invention, $\gamma$ and $\alpha$ are continuously iterated and updated. The initialization condition of iteration may be represented as:

$$\alpha_{init}=\Sigma_{l=1}^{L}\rho_l^* \odot \rho_l/L,$$

$$\gamma_{init,l}=(\tilde{x}_l-\tilde{L}\rho_l)^H(\tilde{x}_l-\tilde{L}\rho_l)/M, l=1,2,\ldots L, \quad (22)$$

where $\rho_l=\sqrt{N}\tilde{L}^H\tilde{x}_l/\|\tilde{L}^H\tilde{L}\|_F$, $\odot$ represents a Hadamard product, and $\|\bullet\|_F$ represents the Frobenius norm. The complexity of calculation in each iteration process is maintained by the inverse operation calculated during the calculation of $\Sigma_l$. When N>M, an updated value of $\Sigma_l$ should be replaced with: $\Sigma_l=\Lambda-\Lambda\tilde{L}^H(\gamma_l I_M+\tilde{L}\Lambda\tilde{L}^H)^{-1}\tilde{L}\Lambda$.

Performance Verification Simulation Experiments for an SBL-Based SSR Source Localization Algorithm A. Calculation of a Head Model and an LFM In the experiment of SSR source localization, the anatomical template MNI/ICBM152 is used in the present invention to implement an unbiased standard estimation of the brain. The spatial information on the surface of the cortex is obtained by separating the interface between the white matter and gray matter included in the MRI template. With the help of the software Brainstorm, the BEM is used in the present invention to compute a 3-layer real head model formed by the scalp, skull, and cortex. In the present invention, 1500 triangle meshes evenly distributed on the surface of the cortex are obtained to represent potential spatial positions of dipoles. Commonly, the current directions of the dipoles are perpendicular to the surface of the cortex. 63-channel EEG electrodes are used to acquire spatially distributed scalp EEG sampling, and an LFM based on the real head model is calculated by using OpenMEEG software.

Figure 2:
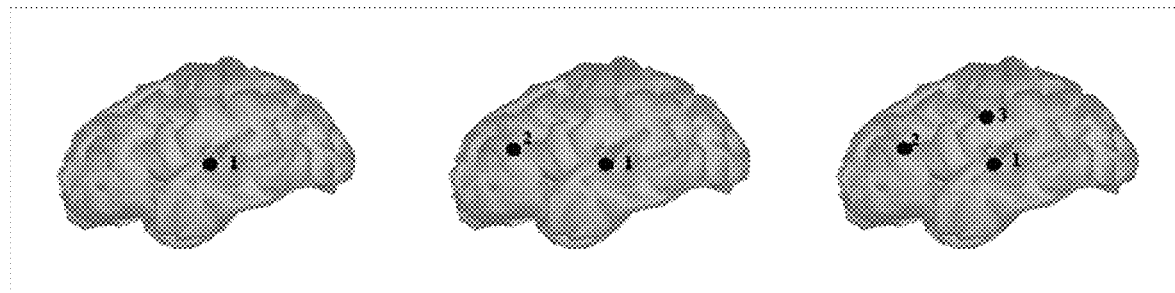
FIG. 2 shows three cases of simulated SSR source distribution in the SBL-based SSR brain source localization method according to the present invention.

B. Simulated Design of an SSR Scalp Record:

To synthesize the SSR scalp record in the head model and test the performance of an SSR source localization method, in the present invention, the distribution of an SSR activation source needs to be designed according to the obtained spatial positions of 1500 meshes on the surface of the cortex, and the source activity of these sources is designed into a signal form of the SSR. As shown in FIG. 2, a total of three source distribution scenarios are designed in the present invention, and the scenarios correspond to cases of one source, two sources, and three sources, respectively. The source numbered 1 is located near the gyri temporalis superior, the source numbered 2 is located near the gyri frontalis medius, and the source numbered 3 is located at the ascending parietal gyri above the lobi temporalis. The sources added for simulation experiments are all located at the left hemisphere.

After the location of an SSR activation source is specified, it is designed in the present invention that the form of an activation source signal is a sinusoidal signal of 40 Hz. That is, $f_0=40$. To simulate spontaneous EEG interference, noise with particular energy is further added in the present invention. After the source signal located on the surface of the cortex being multiplied by an LFM, the SSR scalp record due to simulated synthesis can be obtained. By means of numeric simulation, under each SSR activation source distribution condition, 10 (that is, L=10) SSR scalp records with a length of 10 seconds synthesized in the present invention are used to verify the effectiveness of the SSR source localization algorithm. It is assumed that the power of an SSR source signal and the power of spontaneous EEG are invariant only within a short time, so it is set in the present invention that in the same data segment, the strength of the SSR source signal and the power of spontaneous EEG are fixed values. In different data segments, the strength of the SSR source signal and the strength of EEG noise are variant.

Figure 3:
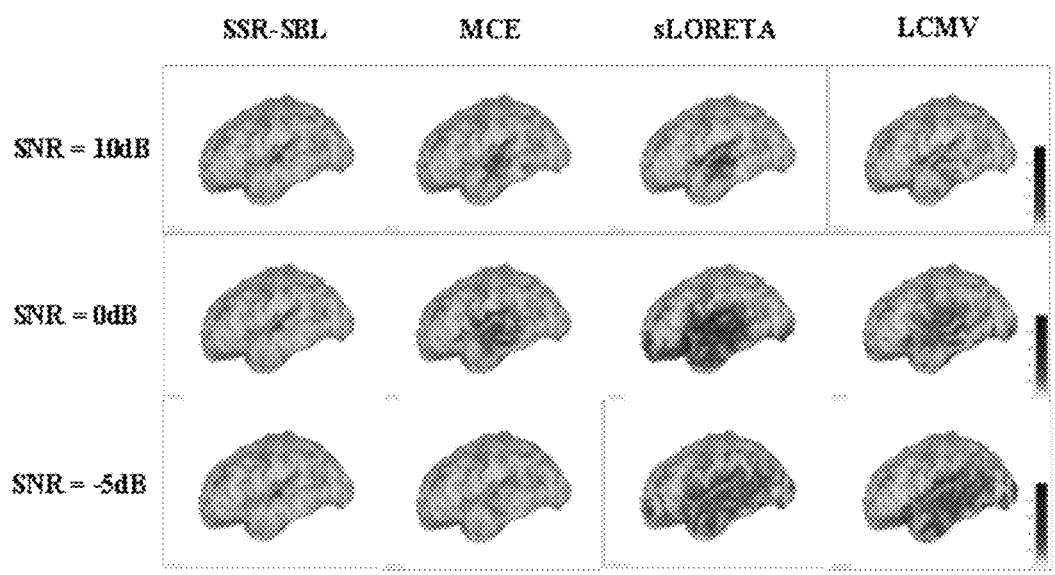
FIG. 3 is a comparison diagram of localization performances when the number of simulated SSR sources is 1 in the SBL-based SSR brain source localization method according to the present invention.
Figure 4:
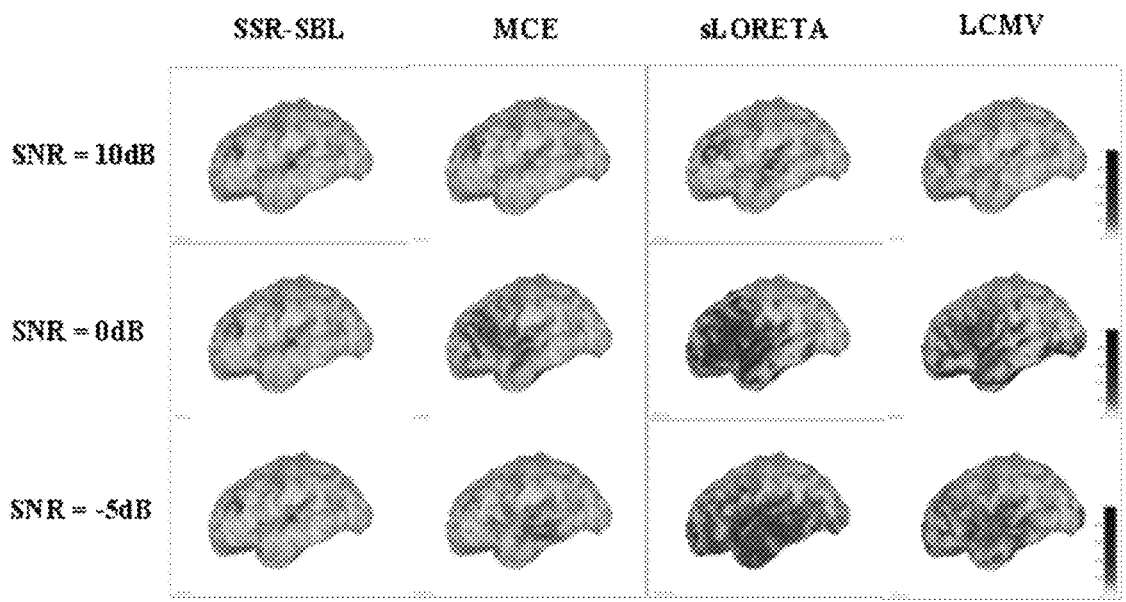
FIG. 4 is a comparison diagram of localization performances when the number of simulated SSR sources is 2 in the SBL-based SSR brain source localization method according to the present invention.
Figure 5:
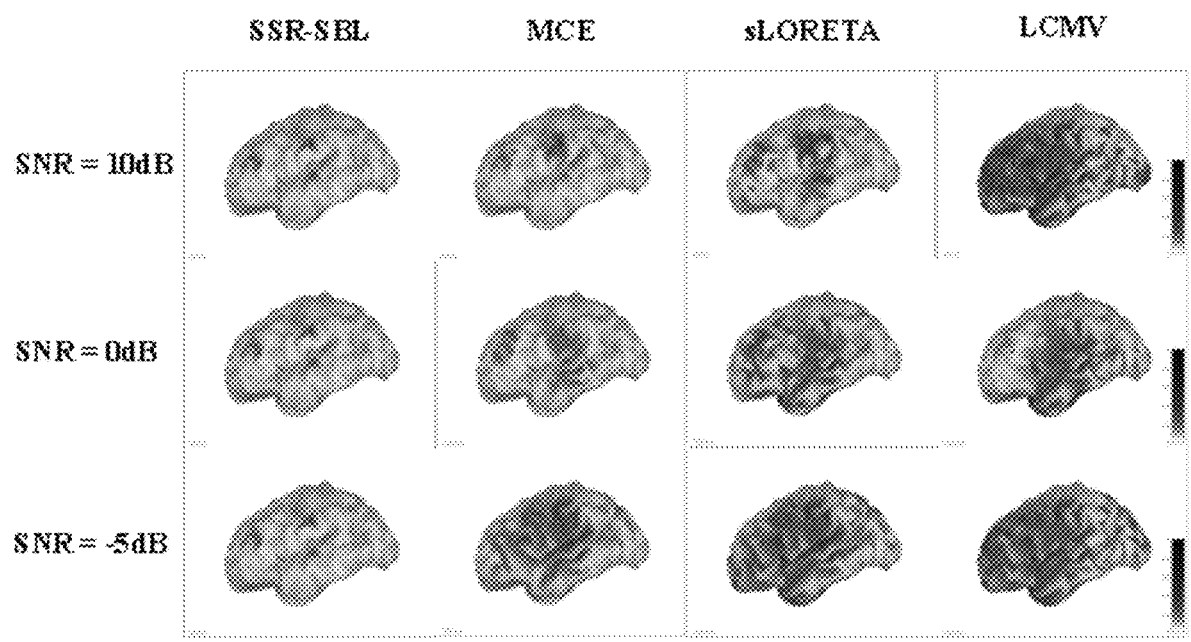
FIG. 5 is a comparison diagram of localization performances when the number of simulated SSR sources is 3 in the SBL-based SSR brain source localization method according to the present invention.

C. SSR Source Localization Result:

For distinguishing from any other SBL methods, SSR-SBL is used in the present invention to represent an SBL-based SSR source localization algorithm provided in the present invention. To prove the performance of the SSR-SBL algorithm, three other linear distributed source localization methods (including MNE, sLORETA, and LCMV beamforming) are used for SSR source localization in the present invention for comparison. FIG. 3, FIG. 4, and FIG. 5 show localization results obtained by various methods in the cases of one, two, and three SSR simulated sources, respectively. A localization result is projected on the cortex in the form of a grayscale diagram. A dark color represents that an SSR source obtained from localization has relatively high strength, and a light gray color represents that an SSR source has relatively low strength. Only results with the top 80% of the total energy of localization results are shown in these drawings in the present invention.

As shown in FIG. 3, in all the methods, the localization result calculated by using the LCMV method is the smoothest. When there is only one activation source, compared with the LCMV method, the MCE method and the sLORETA method can obtain better localization precision. For an MNE method and the sLORETA method, when SNR=10 dB, it may be approximately determined that the locations of sources are lobi temporalis, but the number of sources cannot be accurately given. When SNR=0 dB, the source scale shown by the localization results is far greater than that of the actual size. At this time, it is very difficult to determine the accurate positions of sources. When SNR=−5 dB, the localization results obtained by using the three compared algorithms deviate to the rear half of the brain, and localization results are highly undesirable. In comparison, under the same conditions, the SSR-SBL algorithm provided in the present invention can implement accurate localization performances without localization errors.

In addition to the SSR-SBL algorithm, as the number of simulated sources increases, under the same signal-to-noise ratio condition, the localization effects calculated by using the other three source localization methods become increasingly poor. For example, if the number of SSR simulated sources is 2, when SNR=0 dB, for the localization results calculated by using the MCE method and by using the sLORETA method, the number of sources cannot be determined, let alone the sizes of source distributions. If the number of SSR simulated sources is 2, when SNR=10 dB, compared with the MCE method, the localization results calculated by using the sLORETA method is smoother, and it is very difficult to determine whether two or three activation areas of the SSR sources are shown in the results.

In combination with the foregoing results and analysis, as compared with other linear localization methods, the main distinguishing features of the SSR-SBL algorithm lie in that the localization results calculated by using the SSR-SBL algorithm have very high sparsity, and each separate area in the localization result can be explained as one possible source. At present, the simulation results can prove that when the signal-to-noise ratio is greater than −5 dB, the SSR-SBL source localization method can implement unbiased estimation of the locations of the SSR activation sources.

Application of the SSR-SBL Source Localization Method to Auditory SSR Source Localization As a typical SSR, an auditory SSR has wide clinical application prospects, for example, the application of an auditory SSR to the fields of listening tests, consciousness state assessment, and monitored anesthesia care. The research on auditory SSR sources is of great significance for explaining the clinical application thereof. At present, in a lot of studies, it has been found that an auditory SSR mainly originates from the primary auditory cortex and brain stem, but there are still no precise conclusions. By means of the SSR-SBL source localization algorithm provided in the present invention, the cortex origin of an auditory SSR can be studied. Here, the SSR-SBL algorithm is first applied to a 40-Hz auditory SSR source localization experiment.

In the present invention, nine healthy volunteers with normal listening are recruited, including five men and four women. The volunteers are aged 21±1.89 and have no history of hearing loss and nervous system diseases. With the written permissions of all subjects, an auditory stimulation with an amplitude-modulated sound of a 39.1-Hz sinusoidal waveform is applied to the subjects to evoke a 40-Hz auditory SSR, that is, $f_0=39.1$. Specifically, experimental conditions for evoking the 40-Hz auditory SSR are as follows: Both ears of a subject receive the amplitude-modulated sound of 39.1 Hz with a carrier frequency of 500 Hz as a hearing stimulation, the degree of modulation is 100%, and the density of the sound stimulation is 70 dB. Because the effectiveness of the SSR-SBL source localization algorithm has been verified in simulation experiments, in the present invention it is considered that localization results of the 40-Hz auditory SSR source obtained through the SSR-SBL source localization algorithm are relatively reliable. In real experiments of the 40-Hz auditory SSR in the present invention, a standard 64-channel electrode distribution (except for the ground electrode, the number of effective electrodes is 63, that is, M=63) and BrainVision Recorder software are used to record an auditory SSR. The sampling frequency during recording is 1000 Hz, and at the same time a band-pass filter with a passband frequency of 1 Hz to 300 Hz (12 dB/octave band) and a 50-Hz notch filter are used to suppress noise interference. The EEG acquisition duration for each subject is 200 s. The 200-s EEG data is evenly divided into 10 20-s data segments that are adjacent but do not overlap, that is, L=10. Before carrying out 40-Hz auditory SSR source localization, preprocessing may be performed to increase the signal-to-noise ratio of data.

The preprocessing process includes performing baseline correction, framing, artifact removal, filtering, and time domain averaging on 10 segments of EEG data that correspond to each subject. In the first step, data of the first 5 seconds of an EEG record is used for baseline correction. In the second step, every 1023 data points in the EEG record after baseline correction are grouped into one data frame. The length of each data frame is just 40 complete periods of a sound stimulation signal, and data frames are adjacent but do not overlap. In the third step, a data frame including data point amplitude exceeding 40 uV is eliminated, to perform artifact removal. In the fourth step, the data frames are filtered by using a band-pass filter with a center frequency of 40 Hz and a bandwidth of 10 Hz. Finally, the first 10 data frames in the 10 data segments are kept. Time domain averaging is performed on each data segment to obtain a data segment to be processed $x_l(t)$, where $l=1, 2, \ldots L$. After preprocessing, FFT is performed on $x_l(t)$ to obtain a component $\tilde{x}_l$, corresponding to the stimulation frequency $f_0$, of the data segment, where $(l=1, 2, \ldots L)$, and the size of the vector $\tilde{x}_l$ it is 63×1. In an SSR-SBL model for a single subject, $\tilde{x}_l$ corresponding to the segments of data obtained from a single subject is integrated into an input matrix X with a size of 63×10, where $X=[\tilde{x}_1, \tilde{x}_2, \ldots, \tilde{x}_L]$. In an SSR-SBL model for multiple subjects, the input matrix $X_p$, $p=1, 2, \ldots P$, of size 63×10 corresponding to nine subjects are then further integrated to obtain a joint input matrix X with a size of 63×90 of the multiple subjects, where $X=[X_1, X_2, \ldots, X_P]$. If L=10 and P=9 are known and an LFM L is determined, an iteration process given in the SSR-SBL algorithm can be used to obtain a source distribution result of a 40-Hz auditory SSR iteratively. In the iteration process in the present invention, the error threshold of iteration is set to $\varepsilon=10^{-3}$, and the maximum number of iterations is $N_{iter}=1000$.

The localization result of the SSR-SBL algorithm is shown in FIG. 6. A joint localization result of multiple subjects shows that under binaural stimulation, neurons activated for a 40-Hz auditory SSR are mainly distributed on the temporal lobes of the left and right hemispheres of the brain, and are partially distributed on the front lobe. Compared with the localization result of a single subject, the joint localization result of the plurality of subjects is more stable. It may be assumed that the joint localization result is a combination of localization results of individual subjects, thereby avoiding excessively high noise and excessively low estimation of activation source energy in the localization result of a single subject.

The foregoing embodiments are merely preferred embodiments used to fully describe the present invention, and the protection scope of the present invention is not limited thereto. Equivalent replacements or variations made by a person skilled in the art to the present invention all fall within the protection scope of the present invention. The protection scope of the present invention is as defined in the claims.

What is claimed is:

1. A sparse Bayesian learning (SBL)-based steady-state response (SSR) brain source localization apparatus, comprising: a non-transitory computer readable medium, and an electrode distribution; the non-transitory computer readable medium being programmed to perform:
   step 1: dividing an SSR scalp record acquired by M electrodes into L segments of data, and preprocessing the L segments of data to increase a signal-to-noise ratio, to obtain L data segments $x_l(t)$, wherein L=1, 2, ... L;
   step 2: performing fast Fourier transform (FFT) on $x_l(t)$ corresponding to the L data segments, extracting a complex component $\sim X_L$ of $x_l(t)$ at a stimulation frequency $f_o$, integrating X, corresponding to the L data segments to form a matrix X containing joint SSR distribution information on multiple data segments, wherein $X=[\sim x_1, \sim x_2, \ldots, \sim x_L]$", $(\bullet)^T$ represents transpose, and if there is data of a plurality of subjects, horizontally arranging data matrices of the subjects into one matrix X;
   step 3: setting parameters of an iteration program: an error threshold $\varepsilon$ and a maximum number of iterations Niter, and initializing variables in the iteration program: initializing a sparse support vector $\alpha$ as $\alpha_{init}$, and initializing a spontaneous electroencephalography (EEG)-electrical noise joint power vector $\gamma$ as $\gamma_{init}$;
   step 4: calculating a posteriori mean vector $\mu_L$ and a posteriori covariance matrix $\Sigma_L$ of a source signal corresponding to an $L^{th}$ segment of data by using an SSR data information matrix X, a lead-field matrix (LFM) ~L corresponding to the head model and electrode montage, the sparse support vector $\alpha$, and the spontaneous EEG-electrical noise joint power vector $\gamma$;
   step 5: calculating updated values $\alpha_{new}$ and $\gamma_{new}$, of the sparse support vector $\alpha$ and the spontaneous EEG-electrical noise joint power vector $\gamma$ by using $\mu$, and $\Sigma_L$;
   step 6: determining whether an iteration stop condition 1s satisfied: the number of iterations $$\frac{\|\alpha_{new} - \alpha\|_2}{\|\alpha\|_2} \leq \varepsilon,$$

wherein if the iteration stop condition is not satisfied, make $\alpha=\alpha_{new}$, and $\gamma=\gamma_{new}$, and the process returns to step 4 to continue to perform iteration, or otherwise, iteration ends, and the sparse support vector $\alpha$ is outputted, to obtain a source localization result,
   wherein the non-transitory computer readable medium and the electrode distribution are used to record the SSR scalp record.

2. The SBL-based SSR brain source localization apparatus according to claim 1, wherein preprocessing the data comprises: performing baseline correction and averaging on the overlapped data.

3. The SBL-based SSR brain source localization apparatus according to claim 1, wherein initializing variables in the iteration program comprises:
   (1) initializing the sparse support vector $\alpha$ as $\alpha_{init}=\Sigma_{l=1}^{L}\rho_l^*\odot\rho_l/L$, wherein $\rho_l=\sqrt{N}\tilde{L}^H\tilde{x}_l/\|\tilde{L}^H\tilde{L}\|_F$, $\odot$ represents a Hadamard product, and $\|\bullet\|_F$ represents a Frobenius norm; and
   (2) initializing a spontaneous EEG-electrical noise joint power $\gamma_l$ corresponding to the $l^{th}$ segment of data as $\gamma_{init,l}=(\tilde{x}_l-\tilde{L}\rho_l)^H(\tilde{x}_l-\tilde{L}\rho_l)/M$, wherein l=1, 2, ..., L.

4. The SBL-based SSR brain source localization apparatus according to claim 1, wherein calculating $\mu_l$ and $\Sigma_l$ by using an SSR data information matrix X, an LFM $\tilde{L}$ corresponding to the head model and electrode montage, the sparse support vector $\alpha$, and the spontaneous EEG-electrical noise joint power vector $\gamma$ comprises:

$$\Sigma_l = \Lambda - \Lambda\tilde{L}^H(\gamma_l I_M + \tilde{L}\Lambda\tilde{L}^H)^{-1}\tilde{L}\Lambda, \text{ wherein } \Lambda = \text{diag}(\alpha); \text{ and} \quad (1)$$

$$\mu_l = \gamma_l^{-1}\Sigma_l\tilde{L}^H\tilde{x}_l. \quad (2)$$

5. The SBL-based SSR brain source localization apparatus according to claim 1, wherein calculating updated values $\alpha_{new}$ and $\gamma_{new}$ of the sparse support vector $\alpha$ and the spontaneous EEG-electrical noise joint power vector $\gamma$ by using $\mu_1$ and $\Sigma_l$ comprises:
   (1) $\alpha_{new}[n]=\Sigma_{l=1}^{L}(\Sigma_l[n, n]+\mu_l[n]\mu_l[n]^*)/L$, where n=1, 2, ..., N, $\alpha_{new}[n]$ is an $n^{th}$ element of $\alpha_{new}$, $(\bullet)^*$ represents a conjugate operation, $\Sigma_l[n, n]$ is an $(n, n)^{th}$ element of $\Sigma_l$, and $\mu_l[n]$ is an $n^{th}$ element of $\mu_l$; and (2)

$$\gamma_{new}[l] = \frac{\tilde{x}_l^H \tilde{x}_l - 2Re(\tilde{x}_l^H \tilde{L}\mu_l) + tr[\tilde{L}^H \tilde{L}(\sum_l + \mu_l \mu_l^H)]}{M},$$

where $l=1, 2, \ldots, L$, $\gamma_{new}[l]$ is an $l^{th}$ element of $\gamma_{new}$, and $Re(\bullet)$ and $tr(\bullet)$ are calculating the real part and performing trace operation, respectively.

* * * * *